United States Patent [19]

Müllner et al.

[11] Patent Number: 5,091,553

[45] Date of Patent: Feb. 25, 1992

[54] PROCESS FOR THE PREPARATION OF SUBSTITUTED ISOCYANATES

[75] Inventors: Martin Müllner, Traun; Gerhard Stern, Sonnberg; Erich Schulz, Ansfelden; Markus Rössler, Linz, all of Austria

[73] Assignee: Chemie Linz Gesellschaft m.b.H., Linz, Austria

[21] Appl. No.: 552,696

[22] Filed: Jul. 12, 1990

[30] Foreign Application Priority Data

Jul. 28, 1989 [AT] Austria ................................ 1831/89
Jul. 28, 1989 [AT] Austria ................................ 1832/89
Jul. 28, 1989 [AT] Austria ................................ 1833/89

[51] Int. Cl.$^5$ ........................................ C07C 265/02
[52] U.S. Cl. ...................................... 558/302; 560/338
[58] Field of Search ......................... 558/302; 560/338

[56] References Cited

PUBLICATIONS

CA 109:212501h, Isocyanates Derived from Dienes, Their Preparation, and Curable Compositions therefrom, Waterman et al., (6/88).
CA 72:133406v, Poly(Olefin Isocyanates) from Unsaturated Hydrocarbons and Isocyanaic Acid, Wirpsza, (4/70).

Primary Examiner—Mary C. Lee
Assistant Examiner—Joseph K. McKane
Attorney, Agent, or Firm—Wenderoth, Lind & Ponack

[57] ABSTRACT

Process for the preparation of asymmetrically substituted ureas, carbamates, thiocarbamates or substituted isocyanates by reaction of an adduct of isocyanic acid and a tertiary amine with a primary and secondary amine, an alcohol, a thiol or a compound having one or two non-cumulated olefinic double bonds.

8 Claims, No Drawings

PROCESS FOR THE PREPARATION OF SUBSTITUTED ISOCYANATES

The present invention relates to the preparation of asymmetrically substituted ureas, carbamates, thiocarbamates and substituted isocyanates by reaction of an adduct of isocyanic acid and a tertiary amine in a diluent with primary or secondary amines, alcohols, thiols or a compound which has one or two non-cumulated olefinic double bonds.

The preparation of asymmetrically substituted ureas can be carried out according to Liebig's Annalen der Chemie, Volume 364, pages 129 to 146 by reaction of pure isocyanic acid with a primary or secondary amine in a solvent. Carbamates can be prepared according to Houben-Weyl, Methoden der organischen Chemie (Methods of Organic Chemistry), Supplementary volumes, Volume E4, pages 181 to 189 by reaction of isocyanates with alcohols. It is disclosed in DD 116,551 that isocyanic acid can be reacted with isopropenylbenzene in an organic solvent to give the corresponding isocyanate. However, solutions of free isocyanic acid can only be prepared industrially with difficulty and are difficult to handle so that they can only be employed on the large scale to a limited extent and the isocyanic acid must be liberated from isocyanates for the reaction, polymerization reactions easily occurring.

It has now been found that on addition of primary or secondary amines, alcohols, thiols or compounds which contain one or two non-cumulated olefinic double bonds to a solution or suspension, of an adduct of isocyanic acid with a tertiary amine, which is relatively simple to obtain industrially, asymmetrically substituted ureas, carbamates, thiocarbamates or substituted isocyanates are obtained. Unexpectedly, the isocyanic acid does not have to be set free from the adduct by addition of an acid. The adduct behaves rather like the free isocyanic acid itself.

The invention therefore relates to a process for the preparation of asymmetrically substituted ureas, carbamates, thiocarbamates or substituted isocyanates, which is characterized in that an adduct of isocyanic acid and a tertiary amine is reacted with a primary or secondary amine, an alcohol, a thiol or a compound containing one or two non-cumulated olefinic double bonds in a diluent which is inert under the reaction conditions.

Suitable adducts of isocyanic acid and a tertiary amine are substituted ammonium isocyanates of the formula $R_1R_2R_3N.HNCO$, in which the radicals $R_1$, $R_2$ and $R_3$ denote a cyclic amine moiety, such as, for example, N-alkylpyrrolidine, N-alkylpyrrole, N-alkylpiperidine, pyridine, N-alkylmorpholine or $R_1$, $R_2$ and $R_3$ independently of one another denote straight-chain or branched alkyl, aryl, alkylaryl or arylalkyl groups. Straight-chain or branched alkyl groups are, for example, alkyl groups having 1 to 10 C atoms, such as methyl, ethyl, propyl or butyl groups and their isomers, such as iso-propyl, iso-butyl and tert.butyl groups. Aryl, alkylaryl or arylalkyl groups are phenyl groups which are optionally monosubstituted or polysubstituted by straight-chain or branched alkyl groups having 1 to 5 C atoms and which can be connected to the nitrogen atom via either an aromatic or an aliphatic carbon atom. Examples of such groups are phenyl, tolyl, dimethylphenyl, trimethylphenyl, ethylphenyl, isopropylphenyl, benzyl, methylbenzyl or ethylenephenyl groups. Preferred adducts are those with tertiary amines of the general formula $NR_1R_2R_3$ in which $R_1$, $R_2$ and $R_3$ are identical and denote an alkyl group. Particularly preferred here are alkyl groups having 1 to 5 C atoms, for example trimethylamine, triethylamine, tripropylamine, tributylamine and triisopentylamine. Trimethylamine, triethylamine and triisopentylamine are very particularly preferred.

The adduct of isocyanic acid and tertiary amine can be prepared, for example, from a gaseous mixture of isocyanic acid and ammonia by adding a tertiary amine to this mixture, which has a temperature of 250° to 600° C., bringing the resulting gaseous reaction mixture into contact with an inert diluent and cooling. The starting material required, the gaseous mixture of isocyanic acid and ammonia, is formed during the thermal decomposition of urea, for example according to EP-A-0,124,704.

For the preparation of the compounds according to the invention, the adduct of isocyanic acid and tertiary amine is first introduced in a diluent which is inert under the reaction conditions at temperatures of about $-20°$ C. to room temperature. A primary or secondary amine, an alcohol, a thiol or a compound which contains one or two non-cumulated olefinic double bonds is then added with stirring.

Suitable inert diluents are, for example, aliphatic hydrocarbons, such as pentane, hexane, heptane, aromatic hydrocarbons, such as benzene, toluene, xylene, halogenated aliphatic hydrocarbons, such as methylene chloride, chloroform, carbon tetrachloride, ethyl chloride, ethylene chloride, halogenated aromatic hydrocarbons, such as chlorobenzene, trichlorobenzene, ethers, such as diethyl ether, diisopropyl ether, dibutyl ether, ethyl methyl ether, dioxane, carboxamides, such as dimethylformamide, N-methylpyrrolidone or mixtures of above-mentioned diluents. Aromatic hydrocarbons, halogenated aliphatic hydrocarbons and carboxamides are preferred, and toluene, chloroform or N-methylpyrrolidone are particularly preferred.

Primary and secondary amines are to be understood as meaning those compounds which have one or more amino groups. They may optionally be substituted by other groups which are inert under the reaction conditions. Examples of these are aliphatic, cycloaliphatic or cyclic amines, such as methylamine, ethylamine, hexylamine, hexadecylamine, isopropylamine, isobutylamine, isooctylamine, methylethylamine, cyclohexylamine, pyrrolidine, pyrrole, piperidine, morpholine or dimethylamine, diethylamine, diisopropylamine, ethylenediamine, hexamethylenediamine, 4,4'-diaminodicyclohexylmethane or aromatic amines, such as aniline, nitroanilines, chloroanilines, tolylamines, benzylamine, naphthylamines, phenylenediamines, toluylenediamines and 4,4'-diaminodiphenylmethane.

Alcohols or thiols are understood as meaning compounds which have one or more hydroxyl or mercapto groups. They may optionally be substituted by other groups which are inert under the reaction conditions. Examples of such compounds are aliphatic or cycloaliphatic alcohols or thiols, such as methanol, ethanol, propanol, octadecyl alcohol, isopropanol, isooctanol, cyclohexanol, cyclooctanol, ethylene glycol, glycerol, methylmercaptan, ethylmercaptan, isooctylmercaptan, ethanedithiol, thioglycol, or aromatic alcohols or thiols, such as phenol, nitrophenols, chlorophenols, naphthols, benzyl alcohols, resorcinol, thiophenol, bisphenol A, polyester alcohols and polyether alcohols.

Compounds which contain one or more olefinic double bonds which can optionally be substituted by other groups which are inert under the reaction conditions are, for example, aliphatic or cycloaliphatic compounds, such as ethene, propene, butene, pentene, hexene, hexadecene, isopropene, isobutene, isooctene, cyclohexene, butadiene, octadiene, cyclooctadiene, isoprene, terpenes, or aromatic compounds having an olefinic double bond, such as, for example, styrenes, divinylbenzenes, diisopropenylbenzene, naphthylstyrenes and diphenylethylenes.

The amine, the alcohol, the thiol or the olefin may be added as such, as a gas or a liquid, or together with a diluent as described above, which is gaseous or liquid and inert under the reaction conditions. The amine, the alcohol, the thiol or the olefin can be added in an equivalent amount or in an excess to the adduct of isocyanic acid and tertiary amine. However, it may also be expedient to add the isocyanic acid in excess in order to improve the progress of the reaction.

Preferably, 1 to 7, particularly preferably 1 to 3, mole equivalents of amine, alcohol, thiol or olefin are added per mol of the adduct of isocyanic acid and tertiary amine.

After completion of the addition of the amine, the alcohol, the thiol or the olefin, the mixture is subsequently stirred at room temperature and/or, if desired, heated up to the reflux temperature of the diluent used in order to complete the reaction. If desired, the reaction is also carried out under pressure, it being possible to use pressures up to 20 bar. After cooling, the compound formed crystallizes out of the diluent and is filtered off, or the diluent is evaporated. If desired, further purification can be carried out in a customary manner, such as, for example, by recrystallization, distillation or chromatography.

The process according to the invention yields asymmetrically substituted ureas, carbamates or thiocarbamates or substituted isocyanates in good purity and high yields and thus represents an enrichment of the art.

Example 1

Preparation of Triethylammonium Isocyanate 100 g of urea per hour were continuously introduced into a decomposer. The pyrolysis gases were caused to react in a heatable tube at 320° C. with 255 g of triethylamine per hour, which was introduced in gaseous form. The reaction gases were rapidly cooled to room temperature in a scrubber which was operated with chloroform.

Altogether 213 g (3.5 mol) of urea and 544 g (5.4 mol) of triethylamine were introduced.

Triethylammonium isocyanate was obtained in a yield of 66% of theory, dissolved in chloroform, in this way.

IR: 2160 cm$^{-1}$ (sharp band)

Example 2

14.1 g of dodecylamine (0.076 mol) dissolved in 20 ml of chloroform were added dropwise at room temperature with stirring to 100 ml of a solution of 10 g of triethylammonium isocyanate (0.069 mol) in chloroform, prepared according to Example 1. After completion of the addition, the mixture was subsequently stirred at room temperature for 24 hours and heated to reflux for 1 hour. The solvent was evaporated and the residue was recrystallized from chloroform. 9.45 g, i.e. 60% of theory, of dodecylurea were obtained in this way.

C-H-N analysis:
theoretical: C 68.4%, H 12.3%, N 12.3%
found: C 68.2%, H 12.3%, N 12.3%

Example 3

As described in Example 2, but using 4.9 g of isopropylamine (0.083 mol) and 100 ml of chlorobenzene as the solvent, iso-propylurea was obtained in a yield of 80% of theory after recrystallizing from water.

C-H-N analysis:
theoretical: C 46.7%, H 9.8%, N 27.2%
found: C 47.0%, H 9.6%, N 27.4%

Example 4

As described in Example 2, but using 7.0 g of cyclohexylamine (0.071 mol), cyclohexylurea was obtained in a yield of 70% of theory after recrystallizing from water.

C-H-N analysis:
theoretical: C 59.1%, H 9.9%, N 19.7%
found: C 59.2%, H 9.9%, N 19.7%

Example 5

6.3 g (0.086 mol) of diethylamine were added dropwise to 50 ml of a solution of 6.2 g (0.043 mol) of triethylammonium isocyanate in chloroform, prepared according to Example 1, in such a way that the temperature did not rise above room temperature. After completion of the addition, the mixture was subsequently stirred at room temperature for 24 hours and then heated under reflux for 30 minutes. The reaction mixture was evaporated and the residue was recrystallized from diisopropyl ether, 3.5 g, i.e. 70% of theory, of diethylurea having a melting point of 69°–71° C. being obtained.

Example 6

13.7 g (0.147 mol) of aniline were added dropwise at room temperature with stirring to 100 ml of a solution of 10.6 g (0.0735 mol) of triethylammonium isocyanate in chloroform, prepared according to Example 1. After completion of the addition, the mixture was subsequently stirred at room temperature for 24 hours, after which it was heated to reflux for 30 minutes. The precipitate which was deposited on cooling the reaction mixture was filtered off with suction and washed with a little diethyl ether. A second crystal fraction was obtained by concentrating the mother liquor.

Altogether 6.0 g, i.e. 60% of theory, of phenylurea having a melting point of 143° to 145° C. were obtained.

After recrystallizing a small amount from water the melting point was 146°–148° C.

Example 7

10.1 g (0.1084 mol) of aniline, dissolved in 10 ml of chloroform, were added at −10° C. to 100 ml of a solution of 10.1 g (0.0542 mol) of tri-n-propylammonium isocyanate, prepared according to the procedure described in Example 1. After completion of the addition, the mixture was subsequently stirred at room temperature for 24 hours and heated to reflux for 30 minutes. After cooling the reaction mixture phenylurea crystallized out and was filtered off with suction, washed with a little diethyl ether and dried. 4.8 g of phenylurea, which corresponds to 65% of theory, having a melting point of 144° to 146° C. were obtained in this case.

Example 8

13.5 g (0.1444 mol) of aniline were added dropwise at room temperature to 160 ml of a solution of 16.5 g (0.0722 mol) of tri-n-butylammonium isocyanate in chloroform, prepared according to the procedure described in Example 1. After completion of the addition, the mixture was stirred at room temperature for 24 hours and then heated to reflux for 30 minutes. After cooling, phenylurea precipitated out and was filtered off with suction, washed with a little diethyl ether and dried. 5.9 g of phenylurea, which corresponds to 60% of theory, having a melting point of 142° to 145° C. were obtained in this case.

Example 9

11.8 g (0.1267 mol) of aniline were added dropwise to 130 ml of a solution of 17.2 g (0.0636 mol) of triisopentylammonium isocyanate in chloroform, prepared according to the procedure described in Example 1, in such a way that the temperature did not rise above room temperature. After completion of the addition, the mixture was subsequently stirred at room temperature for 24 hours and then heated to reflux for 30 minutes. After cooling, phenylurea precipitated out and was filtered off with suction, washed with a little ether and dried. 5.1 g of phenylurea, which corresponds to 60% of theory, having a melting point of 143°-145° C. were obtained in this case.

Example 10

As described in Example 6, but using diethyl ether as the solvent, phenylurea having a melting point of 146° to 147° C. was obtained in a yield of 50% of theory after recrystallizing from water.

Example 11

As described in Example 6, but using 9.4 g of 4-chloroaniline (0.0735 mol) and dimethoxyethane as the solvent, 4-chlorophenylurea was obtained in a yield of 50% of theory.

$^1$H-NMR: 6.8–7.0 (s, broad, —NH$_2$); 7.36 (d, aromat. —CH—); 7.51 (d, aromat. —CH—); 9.0 (s, —NH—).

Example 12

1.88 g of ethylenediamine (0.031 mol) were added dropwise at room temperature with stirring to 100 ml of a solution of 10 g of triethylammonium isocyanate (0.069 mol) in 100 ml of N-methylpyrrolidone, prepared according to the procedure described in example i. After stirring at room temperature for 24 hours, the reaction mixture was heated to reflux for one hour, the solvent was evaporated and the residue was recrystallized from water. 3.4 g, i.e. 75% of theory, of ethylenediurea were obtained in this way.

C-H-N analysis:
theoretical: C 32.9%, H 6.9%, N 38.3%
found: C 32.8%, H 7.0%, N 38.2%

Example 13

6.7 g (0.146 mol) of ethanol were added dropwise at room temperature with stirring to 100 ml of a solution of 10.5 g (0.073 mol) of triethylammonium isocyanate in chloroform, prepared according to Example 1, after which the mixture was subsequently stirred at room temperature for 24 hours and then heated to reflux for 1 hour.

The solvent was evaporated and the residue was recrystallized from ethanol, 4.6 g, i.e. 71% of theory, of ethyl carbamate having a melting point of 46°-50° C. being obtained.

Example 14

As described in Example 13, but using 26.6 g of 1-hexadecanol (0.11 mol), hexadecyl carbamate was obtained in a yield of 40% of theory after recrystallizing from chloroform.

$^1$H-NMR: 0.89 (t, —CH$_3$); 1.2–1.6 (m, —CH$_2$—); 4.07 (t, —CH$_2$—O—); 7.2 (s, —NH$_2$).

Example 15

A solution of 7 g (0.066 mol) of benzyl alcohol in 20 ml of chloroform was added dropwise at room temperature with stirring to 100 ml of a solution of 9.5 g (0.066 mol) of triethylammonium isocyanate in chloroform, prepared according to Example 1, after which the mixture was subsequently stirred at room temperature for 12 hours and heated to reflux for 30 minutes.

The solvent was evaporated and the residue was recrystallized from ethanol. 7.0 g, i.e. 70% of theory, of benzyl carbamate having a melting point of 88°-89° C. were obtained in this case.

Example 16

As described in Example 13, but using 10.3 g of 4-chlorophenol (0.080 mol), 4-chlorophenyl carbamate was obtained in a yield of 45% of theory after recrystallizing from methanol/water.

$^1$H-NMR: 5.5 (s, —NH$_2$); 6.8 (d, aryl); 7.2 (d, aryl)

Example 17

18.5 g (0.3 mol) of ethylmercaptan, dissolved in 30 ml of chloroform, were added dropwise at 0° C. with stirring to 120 ml of a solution of 28 g (0.2 mol) of triethylammonium isocyanate in chloroform, prepared according to Example 1, after which the mixture was stirred at this temperature for 1 hour and then subsequently stirred at room temperature for 15 hours. After this, the reaction mixture was heated under reflux for 2 hours. The solvent was distilled off. The oily residue remaining crystallized on cooling and was recrystallized from water.

16 g (0.15 mol), i.e. 75% of theory, of S-ethyl thiocarbamate having a melting point of 99°-102° C. were obtained in this way.

Example 18

As described in Example 17, but using 63 g of 1-octadecylmercaptan (0.22 mol) dissolved in 30 ml of N-methylpyrrolidone, S-octadecyl thiocarbamate was obtained in a yield of 60% of theory.

C-H-N analysis:
theoretical: C 69.2%, H 11.9%, N 4.3%
found: C 69.0%, H 12.0%, N 4.2%

Example 19

As described in Example 17, but using 18.3 g of iso-propylmercaptan (0.24 mol), S-iso-propyl thiocarbamate was obtained in a yield of 70% of theory after recrystallizing from chloroform.

C-H-N analysis:
theoretical: C 40.3%, H 7.5%, N 11.8%
found: C 40.5%, H 7.3%, N 11.8%

Example 20

As described in Example 17, but using 11.3 g of ethanedithiol (0.12 mol), 1,2-di(carbamoylthio)ethane was obtained in a yield of 70% of theory after recrystallizing from chloroform.

$^1$H-NMR 2,91 (—CH$_2$—CH$_2$—); 7,56 (—NH$_2$)
IR: 1650 cm$^{-1}$, 1620 cm$^{-1}$

Example 21

100 ml of a solution of 10 g of cyclohexene (0.12 mol) were added dropwise at 0° with stirring to 100 ml of a solution of 64 g of triisopentylammonium isocyanate (0.24 mol) in chloroform prepared according to example 1, after which the mixture was subsequently stirred at room temperature for 2 hours and the heated to reflux for about 4 hours.

After filtering the resulting cloudy solution, the solvent was distilled off and the residue was distilled at 68° to 73° C., 20 Torr.

7 g of cyclohexyl isocyanate, i.e. 46% of theory, were obtained in this way.

Example 22

3 g (0.025 mol) of alpha-methylstyrene were added dropwise with stirring to 100 ml of a suspension of 11.3 g (0.078 mol) of triethylammonium isocyanate in toluene, prepared according to the procedure described in example 1, after which the mixture was subsequently stirred at room temperature for 3 hours and then heated to reflux for about 4 hours.

A solution of alpha,alpha-dimethylbenzyl isocyanate in toluene was obtained in this way.

After distillation at 40° to 45° C., 1 Torr, alpha,alpha-dimethylbenzyl isocyanate was obtained in a yield of 55% of theory with an n$_D^{25}$ of 1.5048.

Example 23

100 ml of a solution of 10 g of m-diisopropenylbenzene (0.06 mol) in toluene were added dropwise with stirring at 0° C. to a suspension of 16.22 g of triisopentylammonium isocyanate (0.06 mol) in 150 ml of toluene, prepared according to the procedure described in example 1, after which the mixture was subsequently stirred at room temperature for 3 hours and heated to reflux for 3 hours. A solution of m-tetramethylxylene diisocyanate in toluene was obtained in this way.

After distillation at 90° to 95° C., 0.4 Torr, m-tetramethylxylene diisocyanate was obtained in a yield of 50% of theory with an n$_D^{25}$ of 1.5136.

What we claim is:

1. Process for the preparation of substituted isocyanates, comprising reacting an adduct of isocyanic acid and a tertiary amine with a compound having one or two non-cumulated olefinic double bonds in a diluent which is inert under the reaction conditions.

2. Process according to claim 1, comprising employing as the adduct of isocyanic acid and a tertiary amine, a compound of the formula R$_1$R$_2$R$_3$N.HNCO in which R$_1$, R$_2$ and R$_3$ independently of one another denote a straight-chain or branched alkyl group, or an aryl, alkylaryl or arylalkyl group, or R$_1$R$_2$R$_3$N denotes a cyclic amine moiety.

3. Process according to claim 1, comprising employing an adduct of isocyanic acid and a trialkylamine.

4. Process according to claim 1 comprising employing a non halogenated or halogenated, aliphatic or aromatic hydrocarbon, or a carboxamide as the diluent.

5. Process according to claim 4, comprising employing chloroform, toluene or N-methylpyrrolidone as the diluent.

6. Process according to claim 1, comprising carrying out the reaction at temperatures from −20° C. up to the boiling point of the diluent.

7. Process according to claim 1, comprising beginning the reaction at −10° C. and completing at the boiling point of the diluent.

8. Process according to claim 1 comprising completing the reaction under pressure.

* * * * *